(12) United States Patent
Bando et al.

(10) Patent No.: US 8,501,966 B2
(45) Date of Patent: Aug. 6, 2013

(54) METHOD FOR PRODUCING A METHYLENE DISULFONATE COMPOUND

(75) Inventors: Seiji Bando, Hyogo (JP); Takeshi Fujiwara, Hyogo (JP); Hiroyuki Shiraishi, Hyogo (JP); Takehiro Hiyama, Hyogo (JP)

(73) Assignee: Sumitomo Seika Chemicals Co., Ltd., Kako-gun, Hyogo (JP)

( * ) Notice: Subject to any disclaimer, the term of this patent is extended or adjusted under 35 U.S.C. 154(b) by 0 days.

(21) Appl. No.: 13/814,320

(22) PCT Filed: Jul. 27, 2011

(86) PCT No.: PCT/JP2011/067072
§ 371 (c)(1),
(2), (4) Date: Feb. 5, 2013

(87) PCT Pub. No.: WO2012/026266
PCT Pub. Date: Mar. 1, 2012

(65) Prior Publication Data
US 2013/0137881 A1    May 30, 2013

(30) Foreign Application Priority Data
Aug. 25, 2010    (JP) .................................. 2010-187903

(51) Int. Cl.
*C07D 327/00*    (2006.01)
(52) U.S. Cl.
USPC ............................................. 549/19; 549/11

(58) Field of Classification Search
USPC ....................................................... 549/11, 19
See application file for complete search history.

(56) References Cited

U.S. PATENT DOCUMENTS

2009/0137820 A1    5/2009  Hiyama
2010/0041916 A1    2/2010  Okamoto

FOREIGN PATENT DOCUMENTS

| JP | S61-501089 | | 5/1986 |
| JP | 2005-336155 | A1 | 12/2005 |
| JP | 2006-188449 | A1 | 7/2006 |
| WO | WO 85/03075 | A1 | 7/1985 |
| WO | WO 2007/125736 | A1 | 11/2007 |
| WO | WO 2008/032463 | A1 | 3/2008 |

OTHER PUBLICATIONS

International Search Report for International Application No. PCT/JP2011/067072 dated Aug. 30, 2011.

*Primary Examiner* — Kristin Vajda
(74) *Attorney, Agent, or Firm* — Kratz, Quintos & Hanson, LLP

(57) ABSTRACT

The present invention provides a method for producing a methylene disulfonate compound including reacting, in the presence of an acid and a dehydrating agent, a formaldehyde compound with at least one salt of alkanedisulfonic acid selected from the group consisting of alkali metal salts of alkanedisulfonic acid and alkaline earth metal salts of alkanedisulfonic acid each represented by a specific formula. According to the method of the present invention, a methylene disulfonate compound can be obtained in a simple manner at low cost.

5 Claims, No Drawings

METHOD FOR PRODUCING A METHYLENE DISULFONATE COMPOUND

TECHNICAL FIELD

The present invention relates to a method for producing a methylene disulfonate compound.

BACKGROUND ART

Methylene disulfonate compounds are usable as pharmaceutical preparations for treating leukemia in animals, etc.

There are various known methods for producing a methylene disulfonate compound. For example, Patent Literature 1 discloses a method in which sulfonyl chloride is reacted with silver carbonate, and the resulting silver sulfonate is reacted with diiodomethane according to the following reaction formula. In the reaction formula below, R is a hydrogen atom or a methyl group.

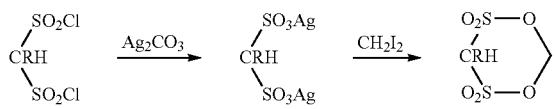

However, such a production method has disadvantages in that the silver carbonate and diiodomethane used are expensive and the reaction is slow.

Patent Literature 2 discloses a method in which alkanedisulfonic acid, etc., is reacted with methylenediacetate, etc., according to the following reaction formula. In the formula below, R' and R" are independently a hydrogen atom or an alkyl group.

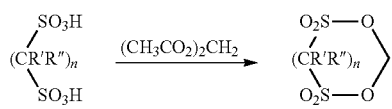

However, such a production method is not industrially suitable because the methylenediacetate, etc., used is expensive and not readily available, and moreover, alkanedisulfonic acid, which is a starting material, is also expensive.

CITATION LIST

Patent Literature

PTL 1: Japanese Unexamined Patent Publication No. S61-501089
PTL 2: Japanese Unexamined Patent Publication No. 2005-336155

SUMMARY OF INVENTION

Technical Problem

The present invention was made in light of the current state of the foregoing prior art. A main object of the present invention is to provide an industrially advantageous method by which a methylene disulfonate compound can be produced in a simple manner at low cost.

Solution to Problem

The present inventors conducted extensive research to achieve the above object. As a result, the present inventors found that metal salts, such as alkali metal salts and alkaline earth metal salts of alkanedisulfonic acid, are inexpensive materials compared to alkanedisulfonic acid, and by reacting such a metal salt as a starting material with a formaldehyde compound in the presence of an acid and a dehydrating agent, a target methylene disulfonate compound can be produced in a simple manner at low cost. Thus, the present inventors accomplished the invention.

Specifically, the present invention provides a method for producing a methylene disulfonate compound as described below.

1. A method for producing a methylene disulfonate compound represented by formula (3)

wherein $R^1$ and $R^2$ are independently a hydrogen atom or a $C_{1-4}$ alkyl group whose hydrogen atom may be substituted with a halogen atom; n is an integer from 1 to 4; and when n is an integer from 2 to 4, n $R^1$s and n $R^2$s may be the same or different;

comprising reacting, in the presence of an acid and a dehydrating agent, a formaldehyde compound with at least one salt of alkanedisulfonic acid selected from the group consisting of alkali metal salts of alkanedisulfonic acid represented by Formula (1),

wherein $R^1$ and $R^2$ are independently a hydrogen atom or a $C_{1-4}$ alkyl group whose hydrogen atom may be substituted with a halogen atom; n is an integer from 1 to 4; and when n is an integer from 2 to 4, n $R^1$s and n $R^2$s may be the same or different; and X is an alkali metal; and alkaline earth metal salts of alkanedisulfonic acid represented by Formula (2)

wherein $R^1$ and $R^2$ are independently a hydrogen atom or a $C_{1-4}$ alkyl group whose hydrogen atom may be substituted with a halogen atom; n is an integer from 1 to 4; and when n is an integer from 2 to 4, n $R^1$s and n $R^2$s may be the same or different; and Y is an alkaline earth metal.

2. The method according to Item 1, wherein the formaldehyde compound is at least one member selected from the group consisting of paraformaldehyde, anhydrous formaldehyde, and trioxane.

3. The method according to Item 1 or 2, wherein the dehydrating agent is phosphorus pentoxide.

4. The method according to any one of Items 1 to 3, wherein the acid is sulfuric acid or fuming sulfuric acid.

5. The method according to any one of Items 1 to 4, wherein the salt of alkanedisulfonic acid is an alkali metal salt of alkanedisulfonic acid represented by Formula (1) wherein X is sodium or potassium.

The method for producing a methylene disulfonate compound of the present invention is explained in detail below.

(1) Starting Material Compound (i) Metal Salt of Alkanedisulfonic Acid

In the present invention, at least one salt of alkanedisulfonic acid selected from the group consisting of alkali metal salts of alkanedisulfonic acid represented by Formula (1),

(1)

and alkaline earth metal salts of alkanedisulfonic acid represented by Formula (2)

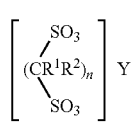

(2)

can be used as a starting material

In Formulae (1) and (2), $R^1$ and $R^2$ are independently a hydrogen atom or a $C_{1-4}$ alkyl group whose hydrogen atom may be substituted with a halogen atom; n is an integer from 1 to 4; X represents an alkali metal; and Y represents an alkaline earth metal.

In the $C_{1-4}$ alkyl group represented by $R^1$ and $R^2$ wherein a hydrogen atom may be substituted with a halogen atom, examples of the halogen atom include a chlorine atom, a bromine atom, a fluorine atom, and the like. Examples of the alkyl group optionally substituted with a halogen atom include a methyl group, an ethyl group, an n-propyl group, an iso-propyl group, an n-butyl group, an iso-butyl group, a sec-butyl group, a tert-butyl group, a chloromethyl group, a bromomethyl group, a fluoromethyl group, a trifluoromethyl group, and the like. Of these, a hydrogen atom, a methyl group, an ethyl group, and an n-propyl group are preferable as $R^1$ and $R^2$.

When n is an integer from 2 to 4 in Formulae (1) and (2), n $R^1$s and n $R^2$s may be the same or different.

Examples of the alkali metal represented by X in Formula (1) include lithium, sodium, potassium, and the like. Examples of the alkaline earth metal represented by Y in Formula (2) include magnesium, calcium, barium, and the like. Of these, an alkali metal salt of alkanedisulfonic acid in which X in Formula (1) is sodium or potassium is preferable.

Examples of the salts of alkanedisulfonic acid represented by Formula (1) or Formula (2) include sodium methanedisulfonate, sodium 1,1-ethanedisulfonate, sodium 1,2-ethanedisulfonate, sodium 1,3-propanedisulfonate, sodium 2,2-propanedisulfonate, sodium 1,4-butanedisulfonate, potassium methanedisulfonate, potassium 1,2-ethanedisulfoate, potassium 1,3-propanedisulfonate, calcium methanedisulfonate, calcium 1,2-ethanedisulfonate, magnesium methanedisulfonate, barium methanedisulfonate, barium 1,2-ethanedisulfonate, barium 1,3-propanedisulfonate, barium 1,4-butanedisulfonate, and the like.

In the present invention, a commercially available salt of alkanedisulfonic acid may be used. Alternatively, a salt of alkanedisulfonic acid synthesized by reacting dichloromethane and an alkali salt of sulfurous acid in an aqueous solvent at 150 to 160° C. with reference to non-patent literature "Recueil des Travaux Chimiques des Pays-Bas, 48, 949-952 (1929)" may be used.

(Ii) Formaldehyde Compound

Examples of the formaldehyde compound usable in the present invention include paraformaldehyde; anhydrous formaldehyde obtained by heating paraformaldehyde; trioxane obtained by treating paraformaldehyde with acid; methylal and like acetalized formaldehydes. Among these, paraformaldehyde, anhydrous formaldehyde, and trioxane are preferable. These formaldehyde compounds may be used singly or in a combination of two or more.

(2) Method for Producing Methylene Disulfonate Compound

In the present invention, using as a starting material at least one salt of alkanedisulfonic acid selected from the group consisting of alkali metal salts of alkanedisulfonic acid represented by Formula (1),

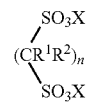

(1)

wherein $R^1$ and $R^2$, and n are the same as above, and alkaline earth metal salts of alkanedisulfonic acid represented by Formula (2)

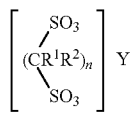

(2)

wherein $R^1$ and $R^2$, and n are the same as above, a formaldehyde compound is reacted, in the presence of an acid and a dehydrating agent, with such a salt of alkanedisulfonic acid to produce a target methylene disulfonate compound represented by Formula (3)

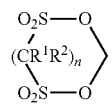

(3)

wherein $R^1$ and $R^2$, and n are the same as above.

In the reaction, the total amount of the formaldehyde compound is preferably about 0.2 to 10 mol and more preferably about 0.3 to 3 mol per mol of the total amount of the salt of alkanedisulfonic acid. When the amount of the formaldehyde compound is too small, the reaction may not be completed. Conversely, when the amount is too large, an effect corresponding to the amount used cannot be obtained, and it is uneconomical.

There is no limitation to the dehydrating agent used in the present invention and, for example, phosphorus pentoxide, phosphorus pentachloride, phosphorus oxychloride, thionyl chloride, acetyl chloride, acetic anhydride, and the like can be used. Among these, phosphorus pentoxide is preferable due to its high reactivity. These dehydrating agents may be used singly or in a combination of two or more.

The total amount of the dehydrating agent is preferably about 0.6 to 10 mol and more preferably about 0.8 to 3 mol per mol of the total amount of the salt of alkanedisulfonic acid. When the amount of the dehydrating agent is too small, the reaction may not be completed. Conversely, when the amount is too large, an effect corresponding to the amount used cannot be obtained, and it is uneconomical.

There is no limitation to the acid used in the present invention and, for example, sulfuric acid, fuming sulfuric acid, hydrogen chloride, nitric acid, fuming nitric acid, methanesulfonic acid, acetic anhydride, and the like, can be used. Among these, sulfuric acid and fuming sulfuric acid are preferable due to their high reactivity and reasonable price. These acids may be used singly or in a combination of two or more.

The total amount of the acid is preferably about 0.1 to 10 mol, and more preferably about 0.5 to 5 mol per mol of the total amount of the salt of alkanedisulfonic acid. When the amount of the acid is too small, the reaction may not be completed. Conversely, when the amount is too large, an effect corresponding to the amount used cannot be obtained, and it is uneconomical.

If necessary, a solvent inactive to the reaction may be used in the present invention. Examples of such inactive solvents include toluene, xylene, monochlorobenzene, dichlorobenzene, trichlorobenzene, hexane, heptane, decane and like hydrocarbon solvents; diethyl ether, ethylene glycol dimethyl ether, dlisopropyl ether, diphenyl ether, tetrahydrofuran, dioxane, cyclopentylmethyl ether, and like ether solvents; dimethylformamide, hexamethyl phosphoric triamide and like amide solvents; ethyl acetate and like acetate solvents; acetonitrile and like nitrile solvents; methyl sulfoxide, sulfolane and like sulfoxide/sulfone solvents; and the like.

The amount of the solvent is generally 1,000 parts by weight or less per 100 parts by weight of the salt of alkanedisulfonic acid, which is used as a starting material.

In the method for producing the methylene disulfonate compound of the present invention, a salt of alkanedisulfonic acid is reacted with a formaldehyde compound in the presence of the aforementioned acid and dehydrating agent. There is no limitation on the specific reaction method. For example, a salt of alkanedisulfonic acid, an acid, and a dehydrating agent may be added and sufficiently stirred in a reactor, and a formaldehyde compound may be added thereto.

The reaction temperature is preferably about 0 to 200° C., and more preferably about 50 to 150° C. Although the reaction time depends on the reaction temperature, it is generally 0.1 to 20 hours.

By the method described above, the methylene disulfonate compound represented by formula (3),

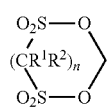
(3)

wherein $R^1$, $R^2$, and n are the same as above, can be obtained.

Examples of the methylene disulfonate compound represented by Formula (3) include methylene methanedisulfonate ($R^1=R^2=H$, n=1), methylene 1,1-ethanedisulfonate ($R^1=CH_3$, $R^2=H$, n=1), methylene 1,2-ethanedisulfonate ($R^1=R^2=H$, n=2), methylene 1,1-propanedisulfonate ($R^1=CH_2CH_3$, $R^2=H$, n=1), methylene 1,2-propanedisulfonate ($R^1=CH_3$ and H, $R^2=H$, n=2), methylene 1,3-propanedisulfonate ($R^1=R^2=H$, n=3), methylene 2,2-propanedisulfonate ($R^1=CH_3$, $R^2=CH_3$, n=1), methylene 1,4-butanedisulfonate ($R^1=R^2=H$, n=4), and the like.

The methylene disulfonate compound obtained by the aforementioned method can be isolated by several methods, such as subjecting a reaction solution to extraction using a solvent or the like, and then conducting crystallization after washing with water, etc; filtering a reaction solution and concentrating the filtrate; subjecting a reaction solution to sublimation refining; etc.

Advantageous Effects of Invention

According to the production method of the present invention, a target methylene disulfonate compound can be easily produced by relatively simple production steps using a readily available inexpensive compound as a starting material. For this reason, the production method of the present invention is industrially advantageous as a method for producing a methylene disulfonate compound.

DESCRIPTION OF EMBODIMENTS

The present invention is explained in detail with reference to Examples below. However, the scope of the present invention is not limited to these Examples.

Example 1

11.0 g (0.05 mol) of sodium salt of methanedisulfonic acid, 5.0 g (0.05 mol) of concentrated sulfuric acid, and 7.2 g (0.05 mol) of phosphorus pentoxide were placed in a four-necked flask equipped with a stirrer, a condenser, a thermometer, and a dropping funnel. 1.6 g (0.05 mol) of 92% paraformaldehyde was added to the mixture while stirring at room temperature. After completion of the addition, the mixture was heated to 120° C. and stirred for one hour. The mixture was then cooled to room temperature and 200 g of methylene chloride was added thereto. After stirring for one hour, insoluble matter was filtered off. The filtrate was concentrated to obtain crystals, and the resulting crystals were dried at 40° C. and 10 mmHg for 6 hours, giving 3.8 g of light brown crystals of methylene methanedisulfonate represented by Formula (3) wherein $R^1$ and $R^2$ are hydrogen atoms, and n is 1. The yield of the resulting methylene methanedisulfonate was 40 mol % relative to sodium salt of methanedisulfonic acid.

The following analysis results confirmed that the resulting light brown crystals were methylene methanedisulfonate.

$^1$H-NMR (400 MHz, CD$_3$CN) δ (ppm): 5.32 (s, 2H), 6.00 (s, 2H).

Example 2

12.6 g (0.05 mol) of potassium salt of methanedisulfonic acid, 2.5 g (0.025 mol) of concentrated sulfuric acid, and 7.2 g (0.05 mol) of phosphorus pentoxide were placed in a four-necked flask equipped with a stirrer, a condenser, a thermometer, and a dropping funnel. 1.6 g (0.05 mol) of 92% paraformaldehyde was added to the mixture while stirring at room temperature. After completion of the addition, the mixture was heated to 120° C. and stirred for one hour. The mixture was then cooled to room temperature and 200 g of methylene chloride was added thereto. After stirring for one hour, insoluble matter was filtered off. The filtrate was concentrated to obtain crystals, and the resulting crystals were dried at 40° C. and 10 mmHg for 6 hours, giving 4.8 g of light brown crystals of methylene methanedisulfonate represented by formula (3) wherein $R^1$ and $R^2$ are hydrogen atoms, and n is 1. The yield of the resulting methylene methanedisulfonate was 51 mol % relative to potassium salt of methanedisulfonic acid.

In the same manner as Example 1, the $^1$H-NMR analysis results confirmed that the resulting light brown crystals were methylene methanedisulfonate.

Example 3

11.0 g (0.05 mol) of sodium salt of 1,2-ethanedisulfonic acid, 2.5 g (0.025 mol) of concentrated sulfuric acid, and 7.2 g (0.05 mol) of phosphorus pentoxide were placed in a four-necked flask equipped with a stirrer, a condenser, a thermometer, and a dropping funnel. 1.6 g (0.05 mol) of 92% paraformaldehyde was added to the mixture while stirring at room temperature. After completion of the addition, the mixture was heated to 120° C. and stirred for five hours. Crystals were obtained in the same manner as Example 1, and the resulting crystals were dried at 40° C. and 10 mmHg for 6 hours, giving 4.7 g of light brown crystals of methylene 1,2-ethanedisulfonate represented by Formula (3) wherein $R^1$ and $R^2$ are hydrogen atoms, and n is 2. The yield of the resulting methylene 1,2-ethanedisulfonate was 46 mol % relative to sodium salt of 1,2-ethanedisulfonic acid.

The following analysis results confirmed that the resulting light brown crystals were methylene 1,2-ethanedisulfonate.

$^1$H-NMR (400 MHz, CD$_3$CN) δ (ppm): 3.80 (s, 4H), 5.61 (s, 2H).

The invention claimed is:

1. A method for producing a methylene disulfonate compound represented by Formula (3)

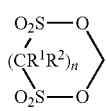

(3)

wherein $R^1$ and $R^2$ are independently a hydrogen atom or a $C_{1-4}$ alkyl group whose hydrogen atom may be substituted with a halogen atom; n is an integer from 1 to 4; and when n is an integer from 2 to 4, n $R^1$s and n $R^2$s may be the same or different;

comprising reacting, in the presence of an acid and a dehydrating agent, a formaldehyde compound with at least one salt of alkanedisulfonic acid selected from the group consisting of alkali metal salts of alkanedisulfonic acid represented by Formula (1),

(1)

wherein $R^1$ and $R^2$ are independently a hydrogen atom or a $C_{1-4}$ alkyl group whose hydrogen atom may be substituted with a halogen atom; n is an integer from 1 to 4; and when n is an integer from 2 to 4, n Ws and n $R^2$s may be the same or different; and X is an alkali metal; and alkaline earth metal salts of alkanedisulfonic acid represented by Formula (2)

(2)

wherein $R^1$ and $R^2$ are independently a hydrogen atom or a $C_{1-4}$ alkyl group whose hydrogen atom may be substituted with a halogen atom; n is an integer from 1 to 4; and when n is an integer from 2 to 4, n $R^1$s and n $R^2$s may be the same or different; and Y is an alkaline earth metal.

2. The method according to claim 1, wherein the formaldehyde compound is at least one member selected from the group consisting of paraformaldehyde, anhydrous formaldehyde, and trioxane.

3. The method according to claim 1, wherein the dehydrating agent is phosphorus pentoxide.

4. The method according to claim 1, wherein the acid is sulfuric acid or fuming sulfuric acid.

5. The method according to claim 1, wherein the salt of alkanedisulfonic acid is an alkali metal salt of alkanedisulfonic acid represented by Formula (1) wherein X is sodium or potassium.

* * * * *